(12) United States Patent
Liu (10) Patent No.: US 9,271,527 B2
(45) Date of Patent: Mar. 1, 2016

(54) ELECTRONIC CIGARETTE AND ELECTRONIC CIGARETTE DEVICE

(71) Applicant: Qiuming Liu, Shenzhen (CN)

(72) Inventor: Qiuming Liu, Shenzhen (CN)

(73) Assignee: HUIZHOU KIMREE TECHNOLOGY CO., LTD., SHENZHEN BRANCH, Shenzhen, Guangdong Province (CN)

( * ) Notice: Subject to any disclaimer, the term of this patent is extended or adjusted under 35 U.S.C. 154(b) by 578 days.

(21) Appl. No.: 13/733,863

(22) Filed: Jan. 3, 2013

(65) Prior Publication Data

US 2013/0340778 A1 Dec. 26, 2013

(30) Foreign Application Priority Data

Jun. 20, 2012 (WO) ............... PCT/CN2012/077235
Aug. 31, 2012 (WO) ............... PCT/CN2012/080843
Aug. 31, 2012 (WO) ............... PCT/CN2012/080846

(51) Int. Cl.
*A24F 47/00* (2006.01)
*A61M 15/06* (2006.01)

(52) U.S. Cl.
CPC ............. *A24F 47/002* (2013.01); *A24F 47/008* (2013.01); *A61M 15/06* (2013.01)

(58) Field of Classification Search
CPC ... A24F 47/002; A24F 47/004; A24F 47/006; A24F 47/00; A24F 47/08; A61M 15/06
See application file for complete search history.

(56) References Cited

U.S. PATENT DOCUMENTS

| | | | | |
|---|---|---|---|---|
| 8,539,959 | B1 * | 9/2013 | Scatterday | 131/361 |
| 2012/0174914 | A1 * | 7/2012 | Pirshafiey et al. | 128/200.14 |
| 2012/0260927 | A1 * | 10/2012 | Liu | A24F 47/008 131/329 |
| 2014/0060527 | A1 * | 3/2014 | Liu | A61M 15/06 128/202.21 |
| 2014/0060556 | A1 * | 3/2014 | Liu | A24F 47/008 131/329 |
| 2014/0190503 | A1 * | 7/2014 | Li | A61M 15/06 131/329 |

OTHER PUBLICATIONS darkknight327, Blaze reviews E-cigarette Decals [https://www.youtube.com/watch?v=uLFm9FLcXjs], Jul. 11, 2010 [downloaded online Jul. 27, 2015].*

* cited by examiner

*Primary Examiner* — Anthony Calandra
(74) *Attorney, Agent, or Firm* — Cheng-Ju Chiang (57) ABSTRACT

This invention discloses an electronic cigarette, which comprises an electronic cigarette main body having a sucking rod and a power rod mutually butted with the sucking rod, and a paper protecting sleeve sleeved around an outer side of the electronic cigarette main body. The sucking rod is provided with an atomizing device for atomizing the liquid smoke to fogged smoke, the sucking rod has one end thereof provided with a sucking nozzle and another end thereof butted with the power rod. The power rod is provided with a battery therein for providing power to the atomizing device. The paper protecting sleeve sleeved and the wooden nozzle cover efficiently enhances touchfeel and mouthfeel of the electronic cigarette; multiple electronic cigarette main bodies or multiple sucking rods enriches electronic cigarette tastes; and the multiple power rods ensures power supply for the electronic cigarette.

13 Claims, 8 Drawing Sheets

ELECTRONIC CIGARETTE AND ELECTRONIC CIGARETTE DEVICE

TECHNICAL FIELD

This invention relates to a field of electronic cigarettes, and particularly to an electronic cigarette and an electronic cigarette device.

DESCRIPTION OF BACKGROUND

Outer main levers of current electronic cigarettes generally use metallic material or plastic material, the touch feel is greatly different from that of the conventional smokes, the simulation is not strong; at the same time, because the electronic cigarettes adopt plastic material or metallic material, the characteristics of metal and plastic materials affect the mouthfeel to a certain extent, the electronic cigarette smokers is difficult to gain the experience of inhaling the conventional cigarettes, which would affect promotion and application of the electronic cigarettes.

At the same time, since the current electronic cigarettes have single taste, and the liquid smoke and batteries in the electronic cigarettes usually can not be fully utilized, the electronic cigarettes have a short life, this is easy to cause unnecessary waste, and smoking expenditures is large for smokers.

SUMMARY

A technical problem the embodiments of the present invention would like to resolve is: to provide an electronic cigarette which has good touchfeel and mouthfeel.

Another technical problem the embodiments of the present invention would like to resolve is: to provide an electronic cigarette device comprising electronic cigarettes with high simulation, for good touchfeel and mouthfeel.

To resolve the above technical problems, an electronic cigarette according to the embodiments of the present invention, comprises an electronic cigarette main body having a sucking rod and a power rod mutually butted with the sucking rod. The sucking rod is provided with an atomizing device for atomizing the liquid smoke to fogged smoke, the sucking rod has one end thereof provided with a sucking nozzle and another end thereof butted with the power rod. The power rod is provided with a battery for providing power to the atomizing device. The electronic cigarette further comprises a protecting sleeve sleeved around an outer side of the electronic cigarette main body, and the protecting sleeve is made of paper material.

Furthermore, the protecting sleeve is configured with a nozzle cover at an end thereof near the sucking nozzle, and the nozzle cover is communicated with the sucking nozzle.

Furthermore, the nozzle cover is made of wooden material.

Furthermore, the protecting sleeve is provided with at least one positioning seat therein, the at least one positioning seat defines a positioning hole coaxial with the protecting sleeve, and the electronic cigarette main body passes through and is fixed into the positioning hole of the at least one positioning seat.

Furthermore, the protecting sleeve is additionally configured with multiple electronic cigarette main bodies and at least one positioning seat therein, and the at least one positioning seat correspondingly defines multiple positioning holes for respectively fixing the electronic cigarette main bodies.

Furthermore, the electronic cigarette main body is additionally configured with multiple sucking rods; a positioning seat is configured at the end of the sucking rods where the sucking nozzle is provided, and the positioning seat correspondingly defines multiple positioning holes for respectively fixing the sucking rods.

Furthermore, the electronic cigarette main body is additionally configured with multiple power rods, and a positioning seat is configured at an end of the power rods away from the sucking rod, the positioning seat correspondingly defines multiple positioning holes for respectively fixing the power rods.

Furthermore, the protecting sleeve is affixed with a sticker on its outer surface.

Furthermore, the electronic cigarette main body is further configured with an illuminant device at an end thereof away from the sucking nozzle, and the protecting sleeve is correspondingly provided with a lampshade to project light from the illuminant device to the exterior.

An electronic cigarette device is further provided in the present invention. The electronic cigarette device comprises an electronic cigarette casing and an electronic cigarette above-described and accommodated in the electronic cigarette casing.

The technical advantages of the embodiments of the present invention is: the paper protecting sleeve sleeved around an outer side of the electronic cigarette main body makes the electronic cigarette to have the feel of a conventional cigarette, and the wooden nozzle cover configured at the sucking nozzle enhances the mouthfeel of the electronic cigarette; multiple electronic cigarette main bodies or multiple sucking rods are configured in the same protecting sleeve to achieve a variety of different flavors of liquid smoke, and enriches electronic cigarette tastes; multiple power rods are configured in the same protecting sleeve, to provide sufficient power, and to ensure a full atomization of the liquid smoke in the electronic cigarette, and to effectively avoid unnecessary waste due to lack of battery power for the electronic cigarette.

DETAILED DESCRIPTION OF THE EMBODIMENTS

It should be noted that, the embodiments and the characteristics in the embodiments can be mutually combined in case of no confliction; the present invention will be described in further detail below through the embodiments in conjunction with the accompanying drawings.

As shown from FIG. 1 to FIG. 10, an electronic cigarette device provided according to an embodiment of the present invention, comprise an electronic cigarette 100 and an electronic cigarette casing 200 for accommodating the electronic cigarette 100.

As shown from FIG. 1 to FIG. 6, the electronic cigarette 100 comprises an electronic cigarette main body 101 and a protecting sleeve 102 sleeved around an outer side of the electronic cigarette main body 101.

The protecting sleeve 102 is a hollow cylinder, and made of paper material, for not only forming a protecting layer at the outer side of the electronic cigarette main body 101, but also providing a touch feeling more similar to conventional paper cigarettes, to comply with the habits of smokers, thereby strengthening the affinity of the electronic cigarette 100, and thus smokers are more likely to accept and like the electronic cigarette 100. In the embodiment of the present invention, the protecting sleeve 102 can be paper materials with certain hardness, for example, kraft paper, writing paper, coated paper, wrapping paper, fiber paper and so on.

As shown from FIG. 2 to FIG. 6, to further improve the simulation of the electronic cigarette 100 and strengthen the touching feeling, the protecting sleeve 102 is affixed with a sticker 103 on its outer surface. An outer side of the sticker 103 can be printed with a same or similar pattern to the appearance of a conventional cigarette; and another side of the sticker 103 affixed to the protecting sleeve 102 is provided with any adhesive which adheres the sticker 102 and the protecting sleeve 102 together.

Figure 9:
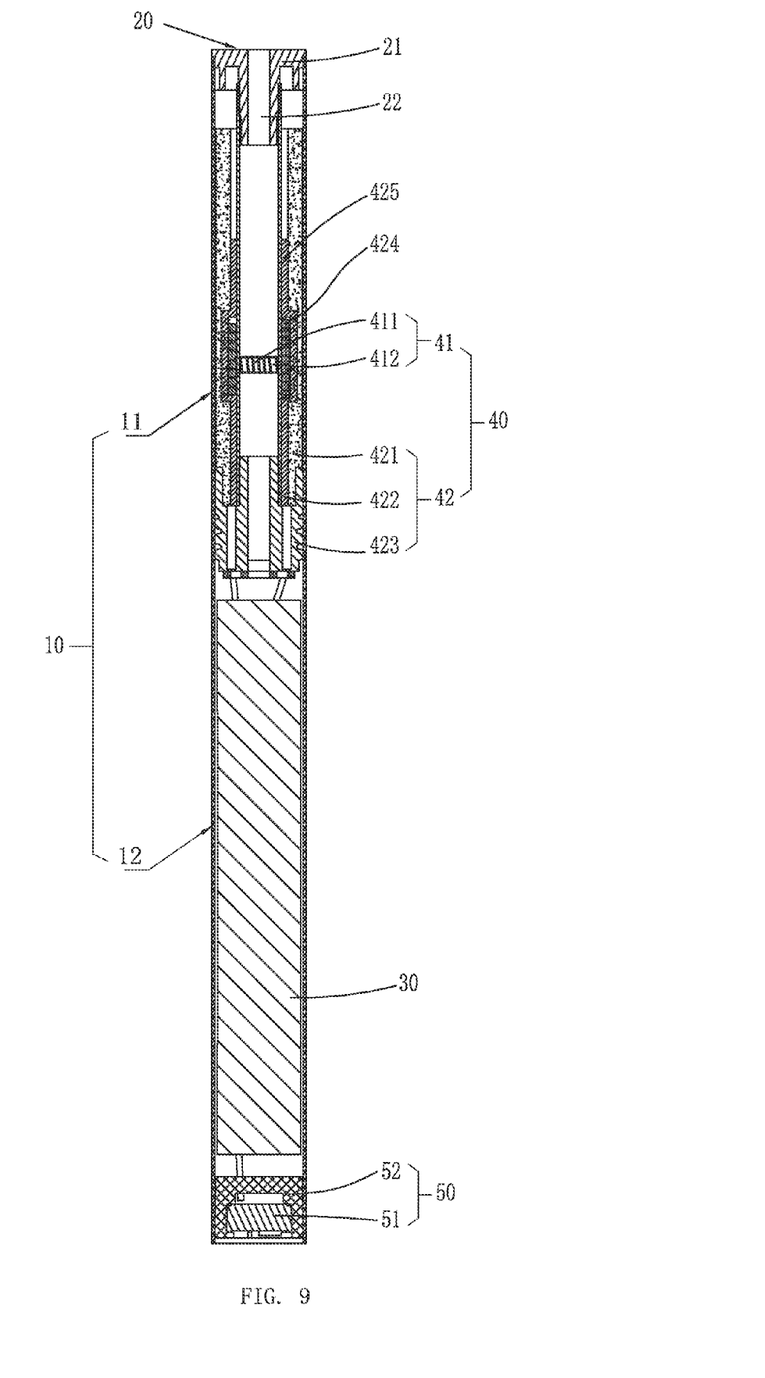
FIG. 9 is a cross-sectional view of an electronic cigarette main body in accordance with an embodiment of the present invention.

The electronic cigarette main body 101 itself can be directly used as a smoke, and can be designed to be any kind of complete electronic cigarette structure. As shown in FIG. 9, in the embodiment of the present invention, the electronic cigarette main body 101 comprises a main rod 10; the main rod 10 has a cylindrical tube-shaped structure, and has a hollow inside to form a receiving chamber for accommodating internal components. Understandably, the main rod 10 can also be designed to have any other tube-shaped structure with hollow receiving chamber, and is not be limited to have cylindrical shape described in the embodiment. In the embodiment, the main rod 10 can be made of stainless steel, but also be made of plastics or other applicable material.

As shown in FIG. 9, the main rod 10 at its one end is provided with a sucking nozzle 20, and at its another end away from the sucking nozzle 20 is provided with a battery 30, therefore, the main rod 10 can be divided into two parts of a sucking rod 11 and a power rod 12, according to an internal component composition of the main rod 10; that is, the electronic cigarette main body 101 is formed jointly by the sucking rod 11 and the power rod 12 mutually butted with the sucking rod 11. In the embodiment, the sucking rod 11 and the power rod 12 is designed to have an undetachable integrated construction. In another embodiment, the sucking rod 11 and the power rod 12 can also be designed to be detachably connected, for example, they are connected by fasteners, plugs, screw thread and so on.

The battery 30 is disposed within the power rod 12, to provide power to functional modules of the electronic cigarette 100. The sucking nozzle 20 is configured at said another end of the sucking rod 11 away from the battery 30. In the embodiment, the sucking nozzle 20 comprises a first nozzle cover 21 disposed at an end portion of the sucking rod 11, and the nozzle cover 21 axially defines a first sucking hole 22.

Figure 3:
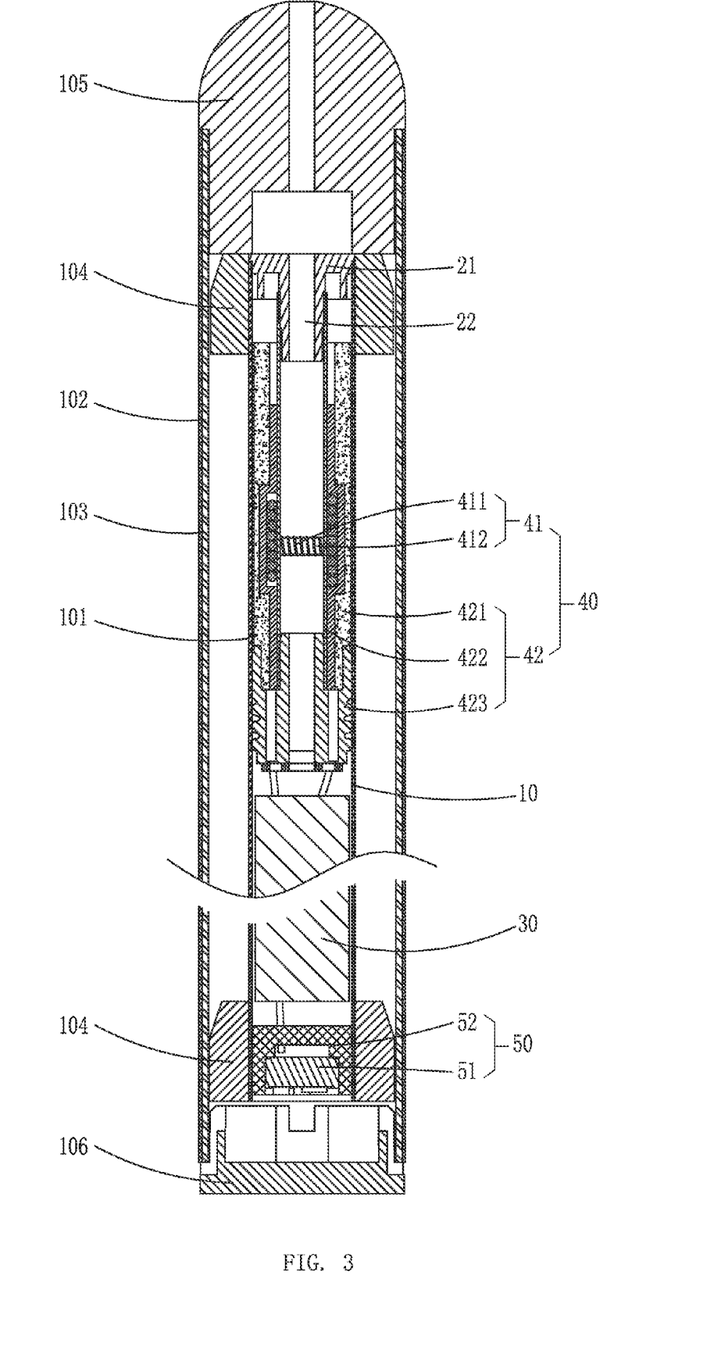
FIG. 3 is a cross-sectional view of the electronic cigarette in accordance with the first embodiment of the present invention.

Please refer to FIG. 3 and FIG. 9, the main rod 10 is further provided with an atomizing device 40 therein for atomizing the liquid smoke into fogged smoke. In the embodiment, the atomizing device 40 is disposed at the sucking rod 11 of the main rod 10, and comprises an atomizer 41 and an atomizing cup 42 for receiving the atomizer 41.

The atomizer 41 is configured for atomizing the liquid smoke into fogged smoke, and comprises a heating wire 411 and a fiber element 412. The heating wire 411 is wound around the fiber element 412, and is fixedly accommodated within the atomizing cup 42 through the fiber element 412. In the embodiment, the fiber element 412 is made of fiberglass or other high temperature resistant fiber material, for absorbing the liquid smoke to be atomized by the heating wire 411; the fiber element 412 has a columned shape.

The atomizing cup 42 comprises a liquid storage component 421, a supporting pipe 422 and an atomizing holder 423, wherein, the liquid storage component 421 and the supporting pipe 422 both are substantially cylindrical and coaxially disposed.

The liquid storage component 421 has a hollow cylindrical construction, which is capable of absorbing and reserving liquid like a sponge, for absorbing and reserving the liquid smoke for facilitating a subsequent atomization by the atomizer 41. In the embodiment, the liquid storage component 421 can be made of a material of fiberglass or absorbent cotton capable of absorbing liquid and reserving liquid. The liquid storage component 421 is sleeved within the main rod 10 and engaged with an inner wall of the main rod 10 by expansion.

The supporting pipe 422 also has a hollow cylindrical construction, and is made of fiberglass. The supporting pipe 422 is sleeved within the liquid storage component 421 to thereby fix the liquid storage component 421 into the main rod 10. The supporting pipe 422 is used for ventilation and supporting the liquid storage component 421.

In the embodiment, the fiber element 412 is radially fixed in the supporting pipe 422 by means of its opposite ends. Outer circumference of the supporting pipe 422 corresponding to a location where the fiber component 412 is fixed is wound with a fiberglass string 424. The fiberglass string 424 is encapsulated with a liquid guiding component 425 abutting against the liquid storage component 421. The liquid guiding component 425 adsorbs the liquid smoke from the liquid storage component 421 and transfers it to the fiber element 412 through the fiberglass string 424 for atomization by the heating wire 411. In another embodiment, instead the supporting pipe 422 can directly defines locking slots therein radially extended through an upper sidewall thereof, and the opposite ends of the fiber element 412 extends out of the supporting pipe 422 via the locking slots and abuts against the inner wall of the liquid storage component 421 to absorb the liquid smoke from the liquid storage component 421 for atomization by the heating wire 411.

The atomizing holder 423 fixedly supports the atomizer 41 and the atomizing cup 42. The atomizing holder 423 and the first nozzle cover 21 respectively seal opposite ends of the atomizing cup 42. The atomizing holder 423 can be made of plastic material, and its shape and size are matched with those of the inner wall of the main rod 10, and is fixed into the main rod 10 by expansion of its outer wall. In the embodiment, the atomizing holder is cylindrical, and therein defines ventholes axially extended therethrough and multiple perforations for the heating wire 411 to pass through.

In the embodiment, the atomizing cup 42 directly utilizes the main rod 10 as its cup main body; understandably, instead the atomizing cup 42 has a cup main body which is independently provided in the main rod 10 and coaxially configured in the main rod 10.

Still refer to FIG. 3 and FIG. 9, the main rod 10 is provided with an atomizing control unit 50 at the end of the main rod 10 away from the sucking nozzle 20, the atomizing control unit 50 is electrically connected with the battery 30 for controlling the atomizing device 40 to be energized or de-energized. The atomizing control unit 50 comprises an atomizing control circuit and an atomizing control switch 51 electrically connected with the atomizing control circuit, and the atomizing control switch 51 is fixed into the main rod 10 through a switch fixing seat 52.

In the embodiment, the atomizing control switch 51 is a sensing switch; specifically, the sensing switch is a capacitance-type sensing switch. When the user uses the electronic cigarette 100 to inhale, the capacitance-type sensing switch changes its capacitance value after sensing the sucking airflow to connect the atomizing control circuit to the power supply, so that the electronic cigarette 100 starts to work. In another embodiment, instead the sensing switch is an airflow sensing switch. When the user inhales through the sucking nozzle 20, a subatmospheric pressure is generated inside the electronic cigarette 100 and thus the airflow sensing switch generates a pulse signal to control the atomizing control circuit to be connected to the power supply.

Since the sensing switch itself is fabricated considerably precisely, and has a special controller built therein, the atomizing control circuit in the embodiment can be directly integrated on the controller within the sensing switch. In another embodiment, instead the atomizing control circuit is integrated on an atomizing control circuit board which is independently configured at an outside of the sensing switch and connected with the sensing switch and the battery 30 respectively.

Certainly, in other embodiment, instead the atomizing control switch 51 can also be a traditional button switch, and the protecting sleeve 102 is correspondingly provided with a pressing member abutting against the button switch, or directly defines an opening for the button switch to outstretch.

Figure 1:
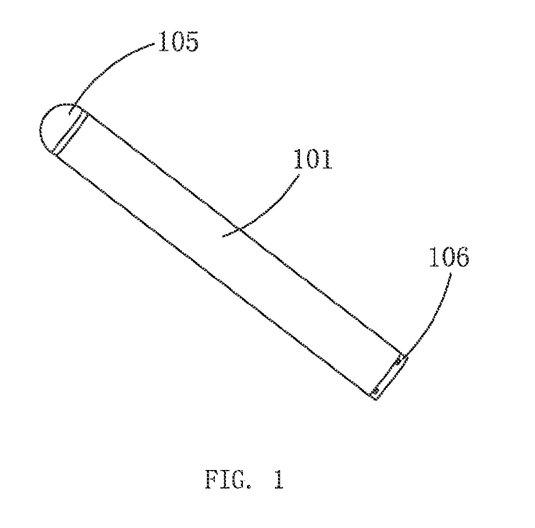
FIG. 1 is an isometric view of an electronic cigarette in accordance with a first embodiment of the present invention.
Figure 2:
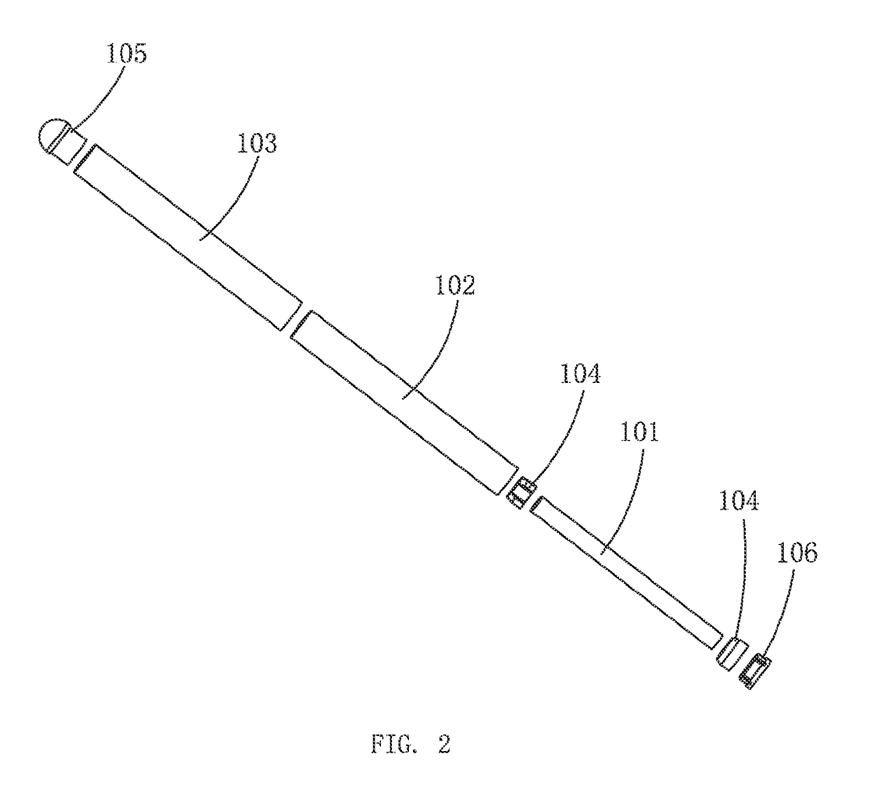
FIG. 2 is an exploded view of the electronic cigarette in accordance with the first embodiment of the present invention.
Figure 4:
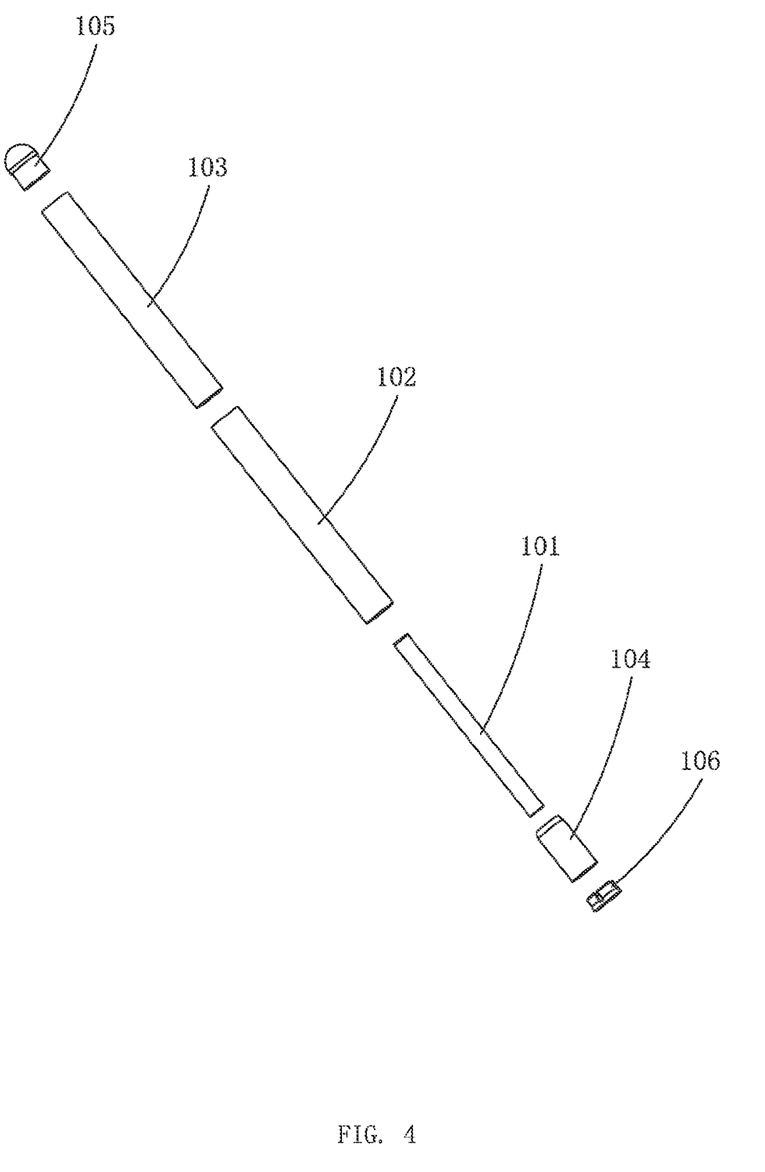
FIG. 4 is an exploded view of an electronic cigarette in accordance with a second embodiment of the present invention.
Figure 7:
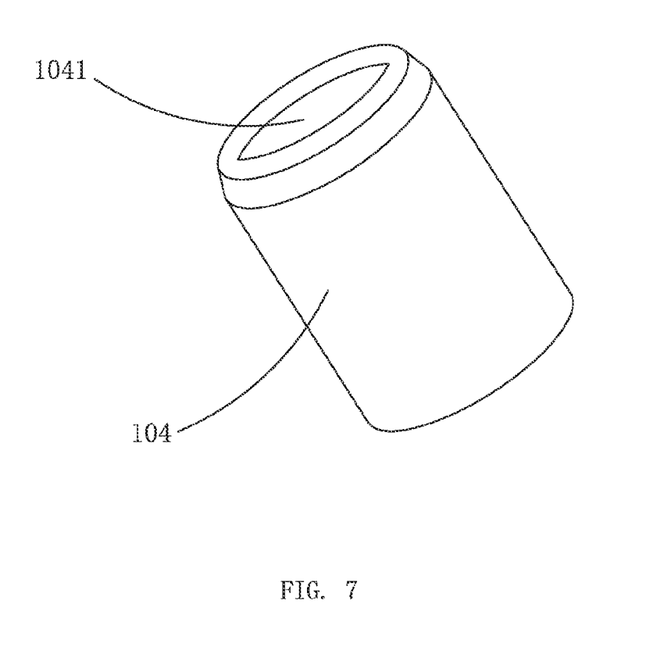
FIG. 7 is an isometric view of a first exemplary positioning seat in accordance with an embodiment of the present invention.
Figure 8:
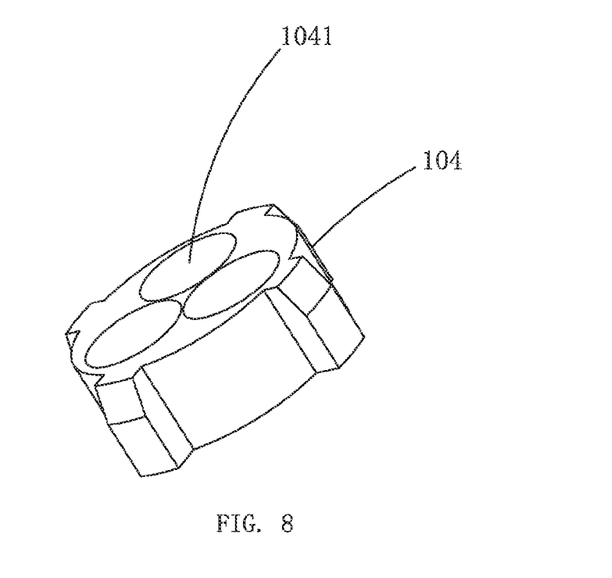
FIG. 8 is an isometric view of a second exemplary positioning seat in accordance with an embodiment of the present invention.

As shown from FIG. 2 to FIG. 4, the protecting sleeve 102 is provided with at least one positioning seat 104 therein, and the electronic cigarette main body 101 is fixed into the positioning seat 102 through the positioning seat 104. As shown in FIG. 7 and FIG. 8, the positioning seat 102 has a cylindrical shape which is coincide with an inner profile of the positioning sleeve 102, and is coaxially configured in the protecting sleeve 102 through its outer wall engaged with an inner wall of the protecting sleeve 102 by expansion. The positioning seat 104 defines a positioning hole 1041 coaxially extended from a central portion thereof, and the electronic cigarette main body 101 passes through and is fixed into the positioning hole 1041.

In the embodiment, the amount and location of the positioning seat 104 depend on an actual requirement. In the embodiment as shown in FIG. 2 and FIG. 3, the protecting sleeve 102 is provided with one electronic cigarette main body 101, and opposite ends of the protecting sleeve 102 are respectively provided with a positioning seat 104. In the embodiment as shown in FIG. 4, the electronic cigarette main body 101 is positioned in the protecting sleeve 102 only through the positioning seat 104 configured at a location away from the sucking nozzle 20. Certainly, the positioning seat 104 can also be disposed at a central portion of the electronic cigarette main body 101. Please refer to FIG. 7, when only one positioning seat 104 is configured in the protecting sleeve 102, the axial length of the positioning seat 104 is appropriately increased, to sufficiently support and position the electronic cigarette main body 101.

Figure 5:
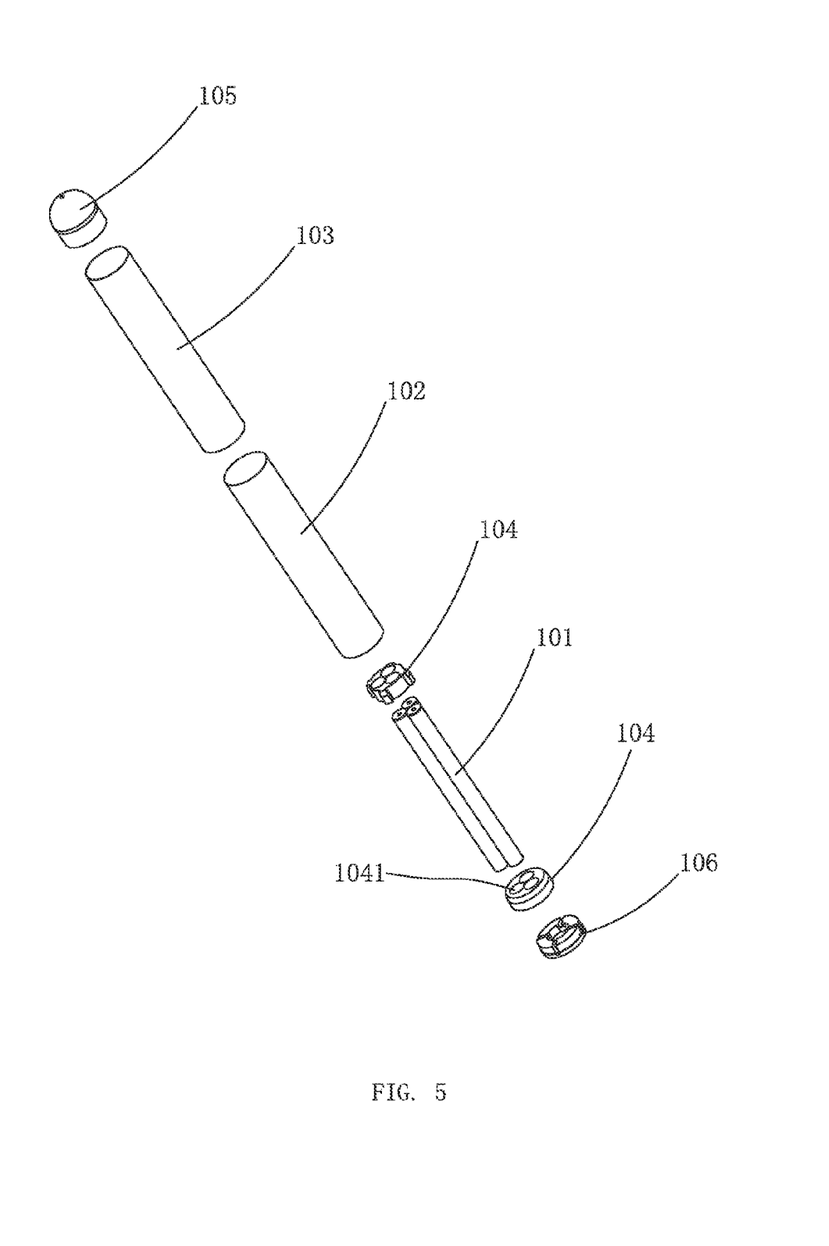
FIG. 5 is an exploded view of an electronic cigarette in accordance with a third embodiment of the present invention.

As shown in FIG. 5, in the embodiment, the protecting sleeve 102 can be provided with multiple electronic cigarette main bodies 101 therein, the multiple electronic cigarette main bodies 101 can accommodate same flavor of liquid smoke, or different flavors of liquid smoke to form a mixed taste, so as to meet the requirements of different smokers. As shown in FIG. 8, when multiple electronic cigarette main bodies 101 are configured in the protecting sleeve 102, the positioning seat 104 is correspondingly configured with positioning holes 1041 for respectively fixing the electronic cigarette main bodies 101.

Figure 6:
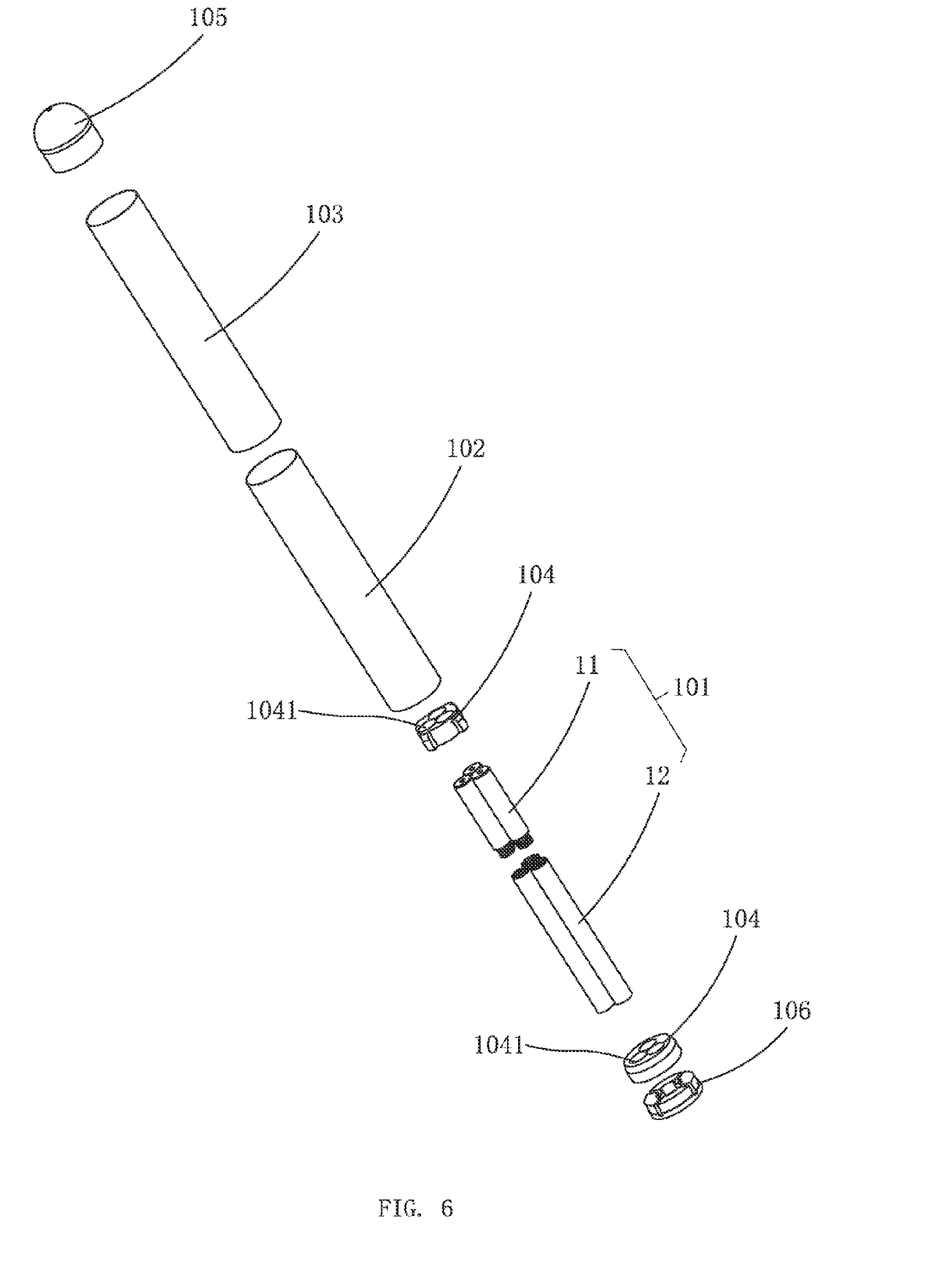
FIG. 6 is an exploded view of an electronic cigarette in accordance with a fourth embodiment of the present invention.

As shown in FIG. 6, in another embodiment, to obtain mixed multiple flavors in one electronic cigarette 100, the electronic cigarette main body 101 can be configured with multiple sucking rods 11, and the sucking rods 11 accommodates different flavors of liquid smoke, so long as the battery 30 in the power rod 12 can provide sufficient power. Certainly, in other embodiment, instead multiple atomizing devices 40 can be directly configured in one sucking rod 11 to obtain mixed multiple flavors of liquid smoke. When the electronic cigarette main body 101 is configured with multiple sucking rods 11, a positioning seat 104 is disposed at the same side of the sucking rods 11 as the sucking nozzle 20 is, and the positioning seat 104 is correspondingly configured with multiple positioning holes 1041 therein for respectively fixing the sucking rods 11, to position the multiple sucking rods 11.

Please still refer to FIG. 6, when the sucking rods 11 have sufficient liquid smoke therein, multiple power rods 12 are required to ensure the batteries 30 in the power rods 12 can provide sufficient power for the sucking rods 11; when multiple power rods 12 are configured in the electronic cigarette main body 101, a positioning seat 104 is configured at the end of the power rods 12 away from the sucking rods 11, and the positioning seat 104 is correspondingly configured with multiple positioning holes 1041 therein for respectively fixing the power rods 12.

Please refer from FIG. 1 to FIG. 6, the protecting sleeve 102 is configured with a second nozzle cover 105 at an end thereof near the sucking nozzle 20, and the second nozzle cover 105 is communicated with the sucking nozzle 20 of the electronic cigarette main body 101. The second nozzle cover 105 axially defines a second sucking hole 1051 communicated with the first sucking hole 22. The second nozzle cover 105 is made of wooden material, to improve the mouthfeel of the electronic cigarette. In the embodiment, the second nozzle cover 105 is specifically made of hickories, walnut, oak, rosewood and so on.

Please still refer from FIG. 1 to FIG. 6, the electronic cigarette main body 101 is further configured with an illuminant device at another end thereof away from the sucking nozzle 20. The illuminant device is used as an indicator of the electronic cigarette 100, and comprises a light-emitting unit electrically connected with the battery 30. The protecting sleeve 102 is correspondingly provided with a lampshade 106 to project the light from the illuminant device to the exterior. In the embodiment, the illuminant device is configured as a red luminous light. When the smoker inhales the electronic cigarette 100, a red aperture similar to that generated during inhaling a traditional cigarette is generated at the end of the electronic cigarette 100 away from the second nozzle cover 105, to improve smokers' visual sense of authenticity.

Understandably, the electronic cigarette 100 in the present invention is not limited to the embodiments as shown in FIG. 1 to FIG. 6, the characteristics in the embodiments can be mutually combined or exchanged in case of no confliction.

Figure 10:
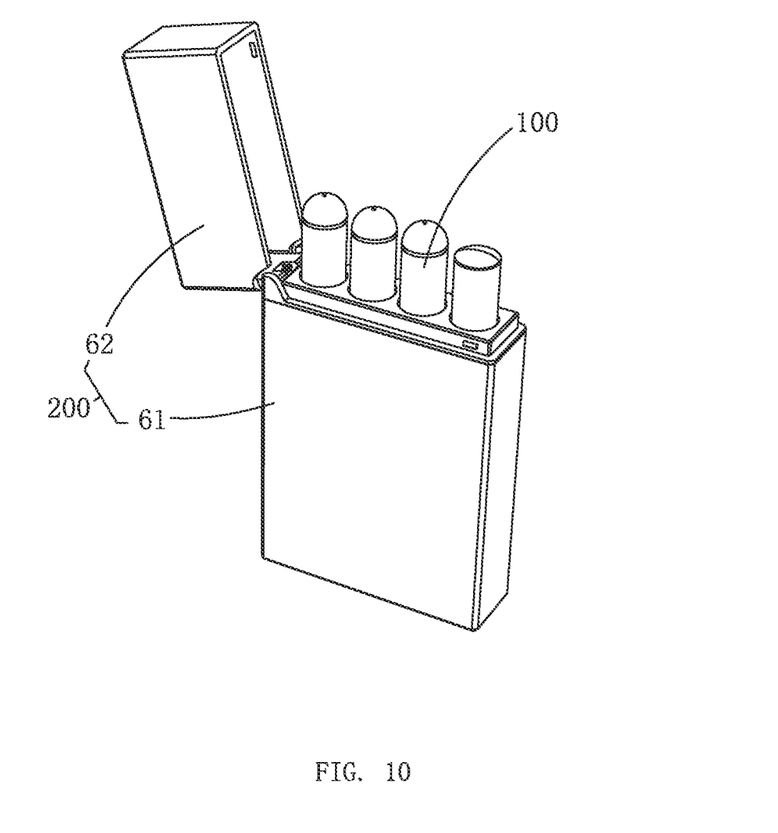
FIG. 10 is an isometric view of an electronic cigarette device in accordance with an embodiment of the present invention.

As shown in FIG. 10, the electronic cigarette 100 generally placed in the electronic cigarette casing 100. The electronic cigarette casing 200 comprises a bottom box 61 for accommodating the electronic cigarettes 100 and a box cover 62 closing the bottom box 61. The bottom box 61 has a square housing structure, certainly, the shape of the bottom box 61 is not limited, and it also can be circular, elliptical, polygonal etc., so long as the box cover 62 may be designed to match with the bottom box 61.

The above-mentioned is only the embodiments of the present invention. It should be noted, for the persons of ordinary skill in this field, improvements and modifications within the spirit of the present invention can be made, and the improvements and modifications should be seemed to be included in the claimed scope of this invention.

What is claimed is:

1. An electronic cigarette, comprising an electronic cigarette main body having a sucking rod and a power rod mutually butted with the sucking rod, the sucking rod being provided with an atomizing device for atomizing the liquid smoke to fogged smoke, the sucking rod having one end thereof provided with a sucking nozzle and another end thereof butted with the power rod, the power rod being provided with a battery therein for providing power to the atomizing device, wherein the electronic cigarette further comprises a protecting sleeve sleeved around an outer side of the electronic cigarette main body;
the protecting sleeve is additionally configured with multiple electronic cigarette main bodies and at least one positioning seat therein, and the at least one positioning seat correspondingly defines multiple positioning holes for respectively fixing the electronic cigarette main bodies.

2. The electronic cigarette as described in claim 1, wherein the protecting sleeve is configured with a nozzle cover at an end thereof near the sucking nozzle, and the nozzle cover is communicated with the sucking nozzle.

3. The electronic cigarette as described in claim 2, wherein the nozzle cover is made of wooden material.

4. The electronic cigarette as described in claim 1, wherein the protecting sleeve is affixed with a sticker on its outer surface.

5. The electronic cigarette as described in claim 1, wherein the electronic cigarette main body is further configured with an illuminant device at an end thereof away from the sucking nozzle, and the protecting sleeve is correspondingly provided with a lampshade to project light from the illuminant device to the exterior.

6. The electronic cigarette as described in claim 1, wherein the protecting sleeve is made of paper material.

7. An electronic cigarette, comprising an electronic cigarette main body having a sucking rod and a power rod mutually butted with the sucking rod, the sucking rod being provided with an atomizing device for atomizing the liquid smoke to fogged smoke, the sucking rod having one end thereof provided with a sucking nozzle and another end thereof butted with the power rod, the power rod being provided with a battery therein for providing power to the atomizing device, wherein the electronic cigarette further comprises a protecting sleeve sleeved around an outer side of the electronic cigarette main body;
the electronic cigarette is configured with one of the following structure that:
the electronic cigarette main body is additionally configured with multiple sucking rods; a positioning seat is configured at the end of the sucking rods where the sucking nozzle is provided, and the positioning seat correspondingly defines multiple positioning holes for respectively fixing the sucking rods; or
the electronic cigarette main body is additionally configured with multiple power rods, and a positioning seat is configured at an end of the power rods away from the sucking rod, the positioning seat correspondingly defines multiple positioning holes for respectively fixing the power rods.

8. The electronic cigarette as described in claim 7, wherein the protecting sleeve is made of paper material.

9. An electronic cigarette device, comprising an electronic cigarette casing and an electronic cigarette accommodated in the electronic cigarette casing, the electronic cigarette comprising an electronic cigarette main body having a sucking rod and a power rod mutually butted with the sucking rod, the sucking rod being provided with an atomizing device for atomizing the liquid smoke to fogged smoke, the sucking rod having one end thereof provided with a sucking nozzle and another end thereof butted with the power rod, the power rod being provided with a battery therein for providing power to the atomizing device, wherein the electronic cigarette further comprises a protecting sleeve sleeved around an outer side of the electronic cigarette main body, and the protecting sleeve is made of paper material;
the electronic cigarette is further configured with one of the following structure that:
wherein the protecting sleeve is additionally configured with multiple electronic cigarette main bodies and at least one positioning seat therein, and the at least one positioning seat correspondingly defines multiple positioning holes for respectively fixing the electronic cigarette main bodies; or
the electronic cigarette main body is additionally configured with multiple sucking rods; a positioning seat is configured at the end of the sucking rods where the sucking nozzle is provided, and the positioning seat correspondingly defines multiple positioning holes for respectively fixing the sucking rods; or
the electronic cigarette main body is additionally configured with multiple power rods, and a positioning seat is configured at an end of the power rods away from the sucking rod, the positioning seat correspondingly defines multiple positioning holes for respectively fixing the power rods.

10. The electronic cigarette device as described in claim 9, wherein the protecting sleeve is configured with a nozzle cover at an end thereof near the sucking nozzle, and the nozzle cover is communicated with the sucking nozzle.

11. The electronic cigarette device as described in claim 10, wherein the nozzle cover is made of wooden material.

12. The electronic cigarette device as described in claim 9, wherein the protecting sleeve is affixed with a sticker on its outer surface.

13. The electronic cigarette device as described in claim 9, wherein the electronic cigarette main body is further configured with an illuminant device at an end thereof away from the sucking nozzle, and the protecting sleeve is correspondingly provided with a lampshade to project light from the illuminant device to the exterior.

* * * * *